United States Patent
Song et al.

(10) Patent No.: US 8,877,687 B2
(45) Date of Patent: Nov. 4, 2014

(54) ASSAYS FOR ANTI-DRUG ANTIBODIES IN THE PRESENCE OF ABUNDANT ENDOGENOUS PROTEIN COUNTERPART OF THE DRUG

(75) Inventors: Sam Shenghua Song, Walpole, MA (US); Arthur J. Kudla, Andover, MA (US); Mark David Moody, Concord, MA (US)

(73) Assignee: Merrimack Pharmaceuticals, Cambridge, MA (US)

( * ) Notice: Subject to any disclaimer, the term of this patent is extended or adjusted under 35 U.S.C. 154(b) by 0 days.

(21) Appl. No.: 13/643,634

(22) PCT Filed: Apr. 26, 2011

(86) PCT No.: PCT/US2011/033916
§ 371 (c)(1),
(2), (4) Date: Dec. 27, 2012

(87) PCT Pub. No.: WO2011/139681
PCT Pub. Date: Nov. 10, 2011

(65) Prior Publication Data
US 2013/0203616 A1    Aug. 8, 2013

Related U.S. Application Data

(60) Provisional application No. 61/327,906, filed on Apr. 26, 2010.

(51) Int. Cl.
*C40B 30/04*        (2006.01)
*G01N 33/68*        (2006.01)

(52) U.S. Cl.
CPC ...... *G01N 33/6854* (2013.01); *G01N 2333/765* (2013.01)
USPC ............................................................. 506/9

(58) Field of Classification Search
None
See application file for complete search history.

(56) References Cited

U.S. PATENT DOCUMENTS

| | | | |
|---|---|---|---|
| 4,618,589 | A | 10/1986 | Jefferis et al. |
| 2007/0202505 | A1 | 8/2007 | Chenchik et al. |
| 2008/0009446 | A1 | 1/2008 | Yu et al. |
| 2011/0059076 | A1 | 3/2011 | McDonagh |

OTHER PUBLICATIONS

International Preliminary Report on Patentability of the International Searching Authority International Application No. PCT/US2011/33916; International Filing Date: Apr. 26, 2011; Date of Mailing Nov. 8, 2012 ; 8 Pages.

Bourdage et al. "An Affinity Capture Elution (ACE) Assay for Detection of Anti-Drug Antibody to Monoclonal Antibody Thereputics in the Presence of High Levels of Drugs" Journal of Immunulogical Methods, 327, pp. 10-17, 2007.

Feldman et al. "Treatment of Relapsed or Reractory Acute Myeloid Leukemia With Humanized Anti-CD33 Monoclonal Antibody HuM195" Lukemia, 17, pp. 314-318, 2003.

International Search Report of the International Searching Authority International Application No. PCT/US2011/33916; International Filing Date: Apr. 26, 2011; Date of Mailing Oct. 4, 2011; 8 Pages.

(Continued)

*Primary Examiner* — Christian Boesen
(74) *Attorney, Agent, or Firm* — Cantor Colburn LLP

(57) ABSTRACT

Methods and kits for detecting antibodies (e.g., anti-drug antibodies) specific for abundant body fluid components are provided. Such methods and kits permit the detection of, for example, human serum albumin in human body fluids, such as blood, plasma and serum.

8 Claims, 10 Drawing Sheets

CP, Assay Sensitivity and Limit Detection of ADA in Sample

(56) References Cited

OTHER PUBLICATIONS

Written Opinion of the International Searching Authority International Application No. PCT/US2011/33916; International Filing Date: Apr. 26, 2011; Date of Mailing Oct. 4, 2011; 7 Pages.
Extended European Search Report and Written Opinion for European Patent Applicaiton No. 11777907.4; Date of Mailing: Aug. 26, 2013; 7 pages.
Gupta et al. "Isolation of Circulating Immune Complexes by Conglutinin and Separation fo Antigen From Dissocated Complexes by Immobilized Protein A" Clin Exp Immunol. (1981) 46, 9-19.
Smith et al. Detection of Antibodies Against Thereapeutic Proteins in the Presence of Residual Therapeutic Protein Using a Solid-Phase Extraction With Acid Dissociation (SPEAD) Sample Treatment Prior to ELISA, Regulatory Toxicology and Pharmacology 49 (2007; pp. 230-237.

SEQUENCE LISTING

<160> NUMBER OF SEQ ID NOS: 2

<210> SEQ ID NO 1
<211> LENGTH: 585
<212> TYPE: PRT
<213> ORGANISM: Human Serum Albumin (HSA)

<400> SEQUENCE: 1

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30
```

```
Gln Cys Pro Phe Glu Asp His Val Lys Leu Val Asn Glu Val Thr Glu
         35                  40                  45
Phe Ala Lys Thr Cys Val Ala Asp Glu Ser Ala Glu Asn Cys Asp Lys
 50                  55                  60
Ser Leu His Thr Leu Phe Gly Asp Lys Leu Cys Thr Val Ala Thr Leu
 65                  70                  75                  80
Arg Glu Thr Tyr Gly Glu Met Ala Asp Cys Cys Ala Lys Gln Glu Pro
                 85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
            115                 120                 125
Asp Asn Glu Glu Thr Phe Leu Lys Lys Tyr Leu Tyr Glu Ile Ala Arg
130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                    165                 170                 175
Cys Leu Leu Pro Lys Leu Asp Glu Leu Arg Asp Glu Gly Lys Ala Ser
                180                 185                 190
Ser Ala Lys Gln Arg Leu Lys Cys Ala Ser Leu Gln Lys Phe Gly Glu
                195                 200                 205
Arg Ala Phe Lys Ala Trp Ala Val Ala Arg Leu Ser Gln Arg Phe Pro
            210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                    245                 250                 255
Arg Ala Asp Leu Ala Lys Tyr Ile Cys Glu Asn Gln Asp Ser Ile Ser
                260                 265                 270
Ser Lys Leu Lys Glu Cys Cys Glu Lys Pro Leu Leu Glu Lys Ser His
            275                 280                 285
Cys Ile Ala Glu Val Glu Asn Asp Glu Met Pro Ala Asp Leu Pro Ser
290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
                340                 345                 350
Tyr Glu Thr Thr Leu Glu Lys Cys Cys Ala Ala Ala Asp Pro His Glu
            355                 360                 365
Cys Tyr Ala Lys Val Phe Asp Glu Phe Lys Pro Leu Val Glu Glu Pro
370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
                420                 425                 430
Val Gly Ser Lys Cys Cys Lys His Pro Glu Ala Lys Arg Met Pro Cys
            435                 440                 445
```

```
Ala Glu Asp Tyr Leu Ser Val Val Leu Asn Gln Leu Cys Val Leu His
            450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
        515                 520                 525
Leu Val Glu Leu Val Lys His Lys Pro Lys Ala Thr Lys Glu Gln Leu
530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu
            580                 585

<210> SEQ ID NO 2
<211> LENGTH: 1755
<212> TYPE: DNA
<213> ORGANISM: Human Serum Albumin (HSA)

<400> SEQUENCE: 2
gatgcacaca agagtgaggt tgctcatcgg tttaaagatt tgggagaaga aaatttcaaa        60
gccttggtgt tgattgcctt tgctcagtat cttcagcagt gtccatttga agatcatgta       120
aaattagtga atgaagtaac tgaatttgca aaaacatgtg tagctgatga gtcagctgaa       180
aattgtgaca atcacttcca tacccttttt ggagacaaat tatgcacagt tgcaactctt       240
cgtgaaacct atggtgaaat ggctgactgc tgtgcaaaac aagaacctga gaaaatgaa        300 tgcttcttgc aacacaaaga tgacaaccca aacctccccc gattggtgag accagaggtt       360
gatgtgatgt gcactgcttt tcatgacaat gaagagacat ttttgaaaaa atacttatat       420
gaaattgcca aagacatcc ttactttat gccccggaac tccttttctt tgctaaaagg       480
tataaagctg cttttacaga atgttgccaa gctgctgata agctgcctg cctgttgcca       540 aagctcgatg aacttcggga tgaagggaag gcttcgtctg ccaaacagag actcaaatgt       600
gccagtctcc aaaaatttgg agaaagagct ttcaaagcat gggcagtggc tcgcctgagc       660
cagagatttc ccaaagctga gtttgcagaa gtttccaagt tagtgacaga tcttaccaaa       720
gtccacacgg aatgctgcca tggagatctg cttgaatgtg ctgatgacag gcggaccttt       780
gccaagtata tctgtgaaaa tcaggattcg atctccagta aactgaagga tgctgtgaa        840 aaacctctgt tggaaaaatc ccactgcatt gccgaagtgg aaaatgatga gatgcctgct       900
gacttgcctt cattagctgc tgattttgtt gaaagtaagg atgtttgcaa aaactatgct       960
gaggcaaagg atgtcttcct gggcatgttt ttgtatgaat atgcaagaag gcatcctgat      1020
tactctgtcg tgctgctgct gagacttgcc aagacatatg aaaccactct agaagaagtgc      1080 tgtgccgctg cagatcctca tgaatgctat gccaaagtgt tcgatgaatt taaacctctt      1140
gtggaagagc tcagaatttt aatcaaacaa actgtgagc ttttttaagca gcttggagag      1200 tacaaattcc agaatgcgct attagttcgt tacaccaaga agtaccccca agtgtcaact      1260
ccaactcttg tagaggtctc aagaaaccta ggaaaagtgg gcagcaaatg ttgtaaacat      1320
```

```
cctgaagcaa aaagaatgcc ctgtgcagaa gactatctat ccgtggtcct gaaccagtta    1380
tgtgtgttgc atgagaaaac gccagtaagt gacagagtca caaaatgctg cacagagtcc    1440
ttggtgaaca ggcgaccatg cttttcagct ctggaagtcg atgaaacata cgttcccaaa    1500
gagtttaatg ctgaaacatt caccttccat gcagatatat gcacactttc tgagaaggag    1560
agacaaatca agaaacaaac tgcacttgtt gagcttgtga aacacaagcc caaggcaaca    1620
aaagagcaac tgaaagctgt tatggatgat ttcgcagctt ttgtagagaa gtgctgcaag    1680
gctgacgata aggagacctg ctttgccgag gagggtaaaa aacttgttgc tgcaagtcaa    1740
gctgccttag gctta                                                    1755
```

ASSAYS FOR ANTI-DRUG ANTIBODIES IN THE PRESENCE OF ABUNDANT ENDOGENOUS PROTEIN COUNTERPART OF THE DRUG

CROSS REFERENCE TO RELATED APPLICATION

This application claims priority from International Application No. PCT/US2011/33916, filed Apr. 26, 2011 which claims priority to U.S. Provisional Patent application 61/327,906, filed Apr. 26, 2010, which is hereby incorporated by reference in its entirety.

TECHNICAL FIELD

The present invention relates generally to methods and kits for detecting anti-drug antibodies in the presence of an abundant endogenous protein counterpart of the drug in the body fluid.

BACKGROUND

It is well known that many therapeutic proteins (e.g., biologic drugs) have immunogenic potential, and administration of therapeutic proteins to a patient sometimes results in the production of antibodies against the therapeutic protein. Such anti-drug antibodies (ADA) may reduce the effectiveness of the therapeutic protein, for example they may bind to or/and neutralize the therapeutic protein, resulting in changes of drug pharmacokinetics or pharmacodynamics that alters drug efficacy. ADA may cause serious side effects, including allergic reactions, cross-reactivity against endogenous proteins, and complement activation. A life-threatening deficiency syndrome can result if ADA cross-reacts with and neutralizes a critical endogenous protein.

To screen for immunogenic activity of biologic drugs, assays for antibodies specific for potential therapeutic proteins, or components thereof, are often used during clinical drug development. Drug interference is regarded as one of the toughest challenges in such immunogenicity testing. For a drug with a long half-life and/or one administered at a high dose or a repeated dose, such as an antibody-based therapy, the ADA usually complexes with the drug, typically making the ADA unavailable for detection. In this situation, acid dissociation is often employed in an attempt to break up the ADA/drug immune complex so as to make the ADA available for detection. When a drug is present at high levels in the blood, it has proven extremely difficult to detect the ADA, even with acid dissociation, and it is often impossible to do so in a reproducible fashion.

Screening test subjects for the production of ADA is an important step in ensuring the safety and efficacy of many therapeutic proteins, and immunogenicity assessment of many therapeutic biologics (drugs comprising proteins) is required by regulatory agencies as part of the pre-clinical and clinical phases of drug development, as well as in the post-market phase to ensure their safety. See, e.g., US Food and Drug Administration (FDA) Draft Guidance for Industry: Assay Development for immunogenicity testing of therapeutic proteins, December 2009.

A variety of assay formats have been used with success to detect anti-drug antibodies, including ELISA (direct, indirect and bridging), radioimmunoassays, electrochemiluminescence, and surface plasmon resonance. The development of such assays, however, is often complicated by interference caused by the presence of the drug.

There is, thus, a need in the art for methods and kits for more accurately and reproducibly detecting anti-drug antibodies in samples (such as human blood fluids) that contain high levels of drug. The present invention fulfills this need, and provides other related advantages.

SUMMARY OF THE INVENTION

Human serum albumin (HSA) is the most abundant protein in human plasma and serum, typically present at a concentration of 35-55 mg/mL, which constitutes nearly half of all plasma protein. HSA, is used for various clinical purposes. It is used for symptomatic relief and supportive treatment in management of shock, burns, hypoprothrombinemia, adult respiratory distress syndrome, cardiopulmonary bypass, acute liver failure, hypotension or shock during renal dialysis, acute nephrosis, hyperbilirubinemia and erythroblastosis fetalis, and as well as for sequestration of protein-rich fluids, erythrocyte resuspension, and as an osmotic adjustment component of vaccines. Because it is a highly abundant endogenous plasma protein, HSA does not trigger an anti-HSA immune response. For this reason (i.e., because it is would not be expected to provoke the generation of ADA), as well as for its effects on pharmacokinetics of fused peptides or polypeptides, HSA or portions or variants thereof, is also used as a component of certain recombinant fusion proteins that are in development as therapeutic agents (drugs).

Despite the known lack of immunogenicity of HSA, the United States Food and Drug Administration has recently, unexpectedly required that patients treated with an HSA fusion protein being clinically developed by the assignee of this application have their serum tested for the development of anti-HSA ADA.

The present invention provides assays and kits for detecting and quantifying anti-drug antibodies specific for a protein or fragment thereof that is present at high levels in a body fluid, such as human serum albumin in human blood fluids, in a reproducible manner. In certain aspects, the present invention provides a method for detecting anti-human serum albumin (HSA) antibodies in a sample (e.g., a serum sample) that comprises immunoglobulin and HSA, comprising:

(a) enriching the immunoglobulin in the sample by incubating the sample with an immunoglobulin affinity substrate so that the immunoglobulin, including any immunoglobulin comprised by immunocomplexes (immunoglobulin bound to antigen) binds to the substrate, followed by elution from the substrate essentially simultaneously with acidic dissociation of any immunocomplexed antigens from the immunoglobulin, to yield an immunoglobulin-enriched, antigen-dissociated sample;

(b) adding labeled HSA and the immunoglobulin-enriched, antigen-dissociated sample to unlabeled HSA that is immobilized on a support, under conditions that result in binding of a detectable amount of labeled HSA to the support if at least 100 ng/mL or at least 125 ng/mL of anti-HSA antibody is present in the sample;

(c) washing the support to remove unbound, labeled HSA; and (d) detecting amount of labeled HSA remaining bound to the support by measuring amount of label remaining bound to the washed support;

wherein the amount of labeled HSA detected is indicative of the level of anti-HSA antibody in the sample.

In a first embodiment the assay yields a signal-to-noise ratio of at least 2.0 if the sample comprises at least 250 ng/mL anti-HSA antibody.

In a second embodiment, the labeled HSA is biotin-conjugated HSA and the detection of an amount of labeled HSA that is bound to the support is achieved by adding a detector—conjugated (e.g., horseradish peroxidase-conjugated) avidin (e.g., streptavidin) to the bound immunocomplexes under conditions that permit the binding of the avidin to the biotin; removing unbound detector-conjugated avidin; detecting amount of bound detector (e.g., by colorimetric readout following addition of tetramethylbenzidine); and therefrom determining the level of labeled HSA that is bound to the support.

In other aspects, the present invention provides methods for reducing interference due to the presence of an endogenous protein counterpart (e.g., HSA) in a sample undergoing an assay. Certain such methods reduce interference due to the presence of HSA in a sample undergoing an assay such as an anti-HSA antibody screening assay, an anti-HSA antibody confirmatory assay, a neutralizing drug antibody assay, a biomarker assay, a drug PK assay, or a drug potency assay. Such methods comprise, prior to performing the assay: (a) enrichment of the immunoglobulin in the sample by incubating the sample with an immunoglobulin affinity substrate so that the immunoglobulin, including any immunoglobulin comprised by immunocomplexes binds to the substrate, followed by elution from the substrate essentially simultaneously with acidic dissociation of any immunocomplexed antigens from the immunoglobulin, to yield an immunoglobulin-enriched, antigen-dissociated sample; and (b) addition of labeled HSA and the immunoglobulin-enriched, antigen-dissociated sample to unlabeled HSA that is immobilized on a support, under conditions that result in binding of a detectable amount of labeled HSA to the support if at least 125 ng/mL of anti-HSA antibody is present in the sample.

In other aspects, methods are provided for improving sensitivity of an assay performed using a sample that comprises an endogenous protein counterpart (e.g., HSA) of a drug. Certain such methods improve sensitivity in an immunogenicity assay, a drug PK assay, a drug potency assay or a biomarker assay. Such methods comprise, prior to performing the assay, (a) enrichment of the immunoglobulin in the sample by incubating the sample with an immunoglobulin affinity substrate so that the immunoglobulin, including any immunoglobulin comprised by immunocomplexes binds to the substrate, followed by elution from the substrate essentially simultaneously with acidic dissociation of any immunocomplexed antigens from the immunoglobulin, to yield an immunoglobulin-enriched, antigen-dissociated sample; and (b) addition of labeled HSA and the immunoglobulin-enriched, antigen-dissociated sample to unlabeled HSA that is immobilized on a support, under conditions that result in of a detectable amount of labeled HSA to the support if at least 125 ng/mL of anti-HSA antibody is present in the sample.

In one embodiment of any of the preceding aspects of the invention, the sample comprises human serum or human plasma. The sample may further comprise a drug comprising HSA or comprising a fragment of at least 50 contiguous amino acids of HSA, and may be obtained from a human to whom the drug was previously administered. In another embodiment, the drug comprises an HSA sequence that is at least 80%, 85%, 90%, 95% or at least 99% identical to the HSA sequence recited in SEQ ID NO:1 or is at least 80%, 85%, 90%, 95% or at least 99% identical to a fragment of at least 50 contiguous amino acids of SEQ ID NO:1. In another embodiment, enriching the sample for immunoglobulin is achieved using an antibody purification resin such as a Protein A/G column, a Protein A column, a Protein G column a 96-well protein A Spin Plate or a 96-well Protein G Spin Plate. In one embodiment, enriching the sample for immunoglobulin results in at least a 100-fold increase in the weight ratio of total IgG to total protein remaining in the sample. In another embodiment the acidic solution has a pH that ranges from 2.5 to 3.5.

In still another embodiment the HSA that is immobilized on the support is covalently bound to a polymeric support, such as a multi-well plate to which the HSA that is immobilized on the support is covalently bound via a photochemical reaction. The HSA may be immobilized on the support by contacting the support with a solution of at least 10 µg/mL HSA at 37° C. for at least 1 hour. Alternatively, the HSA is immobilized on the support by contacting the support with a solution of at least 20 µg/mL HSA at 37° C. for at least 1 hour.

In further aspects, kits are provided that are adapted for detecting a level of anti-HSA antibody in a sample that comprises immunoglobulin and HSA, said kit comprising instructions and, in a container, reagents for:
(a) enriching immunoglobulin in the sample by incubating the sample with an immunoglobulin affinity substrate so that the immunoglobulin, including any immunoglobulin comprised by immunocomplexes binds to the substrate, followed by elution from the substrate essentially simultaneously with acidic dissociation of any immunocomplexed antigens from the immunoglobulin, to yield a highly immunoglobulin-enriched, antigen-dissociated sample;
(b) adding labeled HSA and the immunoglobulin-enriched, antigen-dissociated sample to unlabeled HSA that is immobilized on a support, under conditions that result in indirect binding of a detectable amount of labeled HSA to the support if at least 125 ng/mL of anti-HSA antibody is present in the sample;
(c) washing the support to remove unbound labeled HSA; and
(d) detecting the amount of labeled HSA that remains bound to the support;
wherein the amount of labeled HSA detected is indicative of the level of anti-HSA antibody in the sample;
said reagents comprising one or more of: HSA that is immobilized on a support; labeled HSA; a wash solution; an acidic dissociation solution; and a control sample comprising immunoglobulin, HSA, and anti-HSA antibody.

In still another aspect, a method is provided for preparing a sample for measurement of a level of anti-HSA antibody in the sample, said sample comprising immunoglobulin and HSA, the method comprising:
(a) enriching the immunoglobulin in the sample by incubating the sample with an immunoglobulin affinity substrate so that the immunoglobulin, including any immunoglobulin comprised by immunocomplexes binds to the substrate, followed by elution of immunoglobulin from the substrate essentially simultaneously with acidic dissociation of any immunocomplexed antigen from the immunocomplexes, to yield an immunoglobulin-enriched, antigen-dissociated sample suitable for measurement of a level of anti-HSA antibody therein, wherein the limit of detection of said level in the enriched sample is at least 100 ng/mL of anti-HSA antibody.

In a first embodiment the sample comprises human serum or human plasma. The sample may further comprise a drug comprising HSA or a fragment of at least 50 contiguous amino acids thereof, and may be obtained from a human to whom the drug was previously administered. In another embodiment, the drug comprises an HSA sequence that is at least 90% identical to the HSA sequence recited in SEQ ID NO:1.

In a second embodiment the enriching the sample for immunoglobulin is achieved using an antibody purification resin. The resin may be comprised in a protein A/G column, a protein A column, a protein G column, a multi-well (e.g., 96 well) protein A/G spin plate, a multi-well protein A spin plate, or a multi-well protein G spin plate. The enriching the sample for immunoglobulin may result in at least a 100-fold increase in the weight ratio of total IgG to total protein remaining in the sample. In some embodiments the acidic solution has a pH that ranges from 2.5 to 3.5.

These and other aspects of the present invention will become apparent upon reference to the following detailed description.

DESCRIPTION OF THE SEQUENCE LISTING

Figure 1:
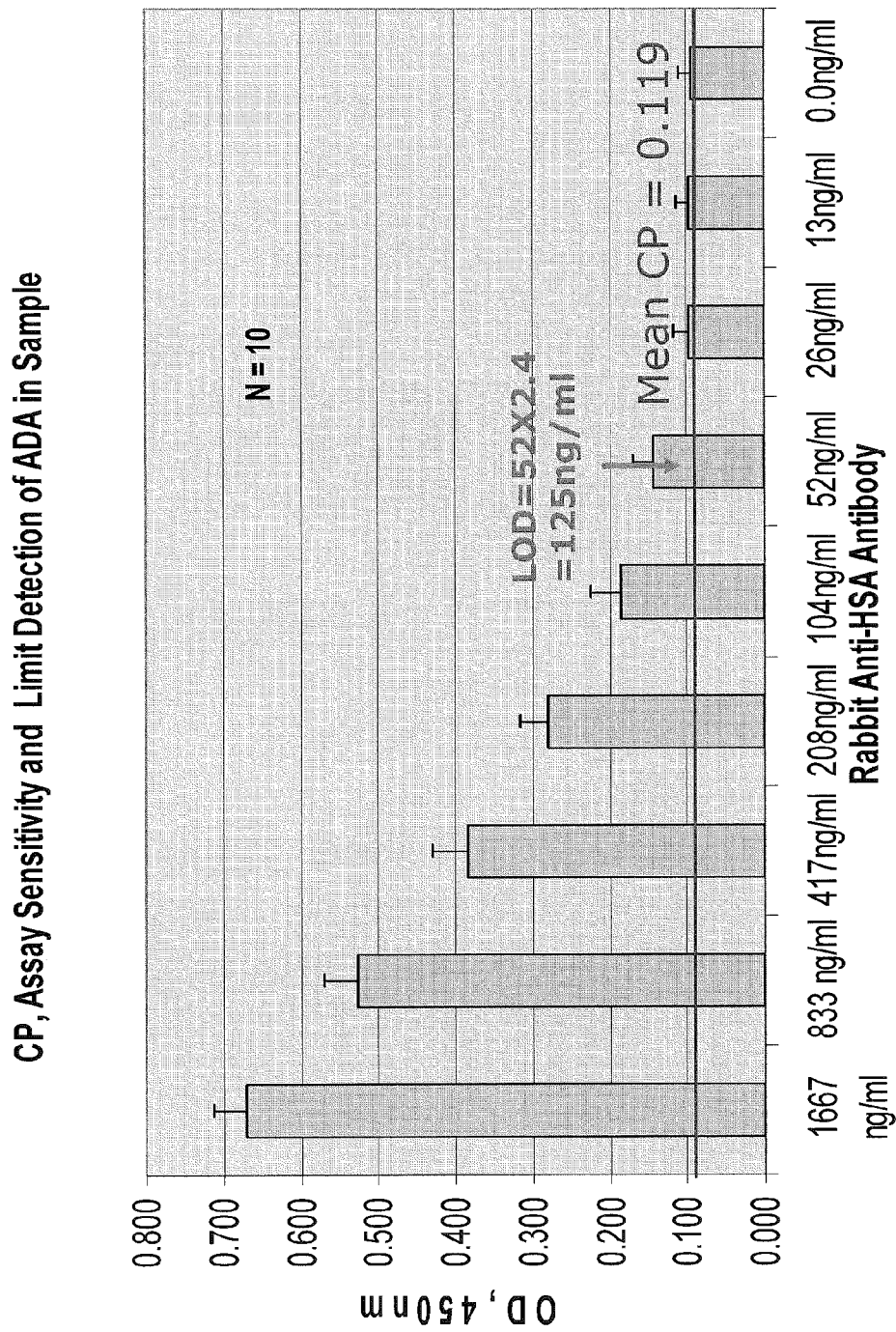
FIG. 1 is a graph showing the optical density (OD) at 450 nm for samples of normal human serum to which various amounts of rabbit anti-HSA antibody have been added prior to sample preparation and assay as described in Examples 1 and 2.

SEQ ID NO:1 is the amino acid sequence of HSA.
SEQ ID NO:2 is the nucleic acid sequence of HSA.

DETAILED DESCRIPTION OF THE INVENTION

The present invention is, in part, directed to methods and kits for detecting antibodies specific for abundant body fluid components (i.e., components that are present in the fluid at levels that are high enough to interfere with conventional assays). While the invention is described herein with reference to the detection of anti-HSA antibodies in human blood fluids, such as plasma and serum, it will be readily apparent that the invention extends to the detection of anti-drug antibodies (ADA) specific for other abundant blood fluid components (e.g., alpha globulins, beta globulins, fibrinogen, transferrin, alpha-1 antitrypsin, haptoglobin), blood fluid components of other species, and abundant components of other body fluids. Certain methods provided herein for detecting anti-HSA antibodies generally comprise a sample preparation procedure as described herein, followed by a bridging ELISA assay, in which the sample to be tested is contacted with both immobilized antigen (antigen bound to a support) and labeled antigen in solution, such that antibodies within the sample form immunocomplexes with both the immobilized antigen and the labeled antigen. Through the formation of such immunocomplexes, the antibodies and labeled antigen are bound to the support. The bound antibodies are then detected based on detection of bound label. It has been found, within the context of the present invention, that the high levels of HSA in the samples to be tested do not interfere with this assay provided that the assay and the sample preparation are performed as described herein.

Briefly, methods for detecting anti-HSA antibodies provided herein generally comprise: (1) one or more sample preparation steps that effectively remove HSA, enrich the sample for immunoglobulin and dissociate immunocomplexed antigens from antibodies; and (2) a bridging ELISA in which labeled (e.g., biotin-conjugated) HSA and the immunoglobulin-enriched, dissociated sample are added to immobilized HSA (e.g., HSA that is bound to the wells of a 96-well plate or other suitable support), under conditions that permit the formation of immunocomplexes comprising labeled HSA, immobilized HSA and an antibody; and bound labeled HSA is subsequently detected.

As used herein, an "anti-HSA antibody" is an antibody that binds immunospecifically to HSA. For standards and positive controls, anti-HSA antibodies may be prepared by well-known techniques, and are commercially available from suppliers such as ABCAM (Cambridge, Mass.), ImmuneChem Pharmaceuticals (Burnaby, Canada) and Novus Biologicals (Littleton, Colo.).

Testing Samples

As noted above, the sample to be assayed may be any body fluid or fraction thereof that comprises immunoglobulin and HSA. Typical samples are blood fluids, such as plasma or serum. Such blood fluids may be prepared from blood obtained from a patient or test subject by standard methods. In certain embodiments, the blood fluid further comprises at least one drug. For example, the blood fluid may be obtained from a patient who has been treated with a drug (e.g., a human to whom the drug was previously administered).

In this context, a drug may be an approved pharmaceutical agent or may be a candidate pharmaceutical agent undergoing experimentation or clinical testing. Certain drugs are proteins that comprise an HSA sequence, or portion or variant thereof.

For example, an HSA sequence is an amino acid sequence that is at least 95% identical to the HSA amino acid sequence recited in SEQ ID NO:1; or an amino acid sequence that comprises at least 50 consecutive amino acids of the HSA sequence of SEQ ID NO:1, or that comprises an amino acid sequence that is at least 95% identical to 50 consecutive amino acids of SEQ ID NO:1. Certain drugs comprise the HSA sequence recited in SEQ ID NO:1 with from 0 to 10 amino acid substitutions. HSA sequences may be prepared, for example, by expressing a polynucleotide that encodes the HSA sequence (e.g., the polynucleotide sequence provided in SEQ ID NO:2).

Sample Preparation

The purpose of the sample preparation is to remove HSA, enrich the sample for immunoglobulin and dissociate immunocomplexed HSA from anti HSA-antibodies. A sample is said to be "enriched for immunoglobulin," in the context of the present invention, if the weight ratio of total immunoglobulin to total protein increases by at least a factor of 50; in certain embodiments, the weight ratio of total immunoglobulin to total protein increases by at least a factor of 100, 200 or 500. The enrichment effectively removes a substantial portion of the endogenous HSA (e.g., at least 99%), along with other proteins, from the sample; accordingly, the enrichment process also serves to remove HSA from the sample. The extent of enrichment may be determined using standard methods. Total protein may be determined, for example, by a Bradford assay, Lowry assay or other known technique. Total immunoglobulin may be determined, for example, using a sandwich ELISA in which samples are reacted with an anti-IgG antibody, or using an immunoprecipitation assay (e.g., as described in U.S. Pat. No. 4,618,589, which is hereby incorporated by reference for its teachings regarding immunoprecipitation assays). In certain embodiments, the enrichment for immunoglobulin is at least as great as the enrichment achieved when a sample is treated as described in Example 1, herein; in other embodiments, the enrichment for immunoglobulin is approximately the same as (e.g., within about 10% of) the enrichment achieved by treatment as described in Example 1, herein. Enrichment may be accomplished by any standard technique; the use of an immunoglobulin affinity substrate (e.g., an antibody purification resin) is generally convenient.

The phrase "dissociate immunocomplexed HSA from anti-HSA antibodies" refers to the separation of antigen (HSA) from immunocomplexes with antibody in the sample. In general, dissociation is achieved by treatment with acid (e.g., treatment with about 300 mM acetic acid for about half hour to an hour, or treatment with a buffer solution having a pH ranging from about 2 to about 4, or from 2.5 to 3.5). Dissociation is generally sufficient if it results in an assay that is able to detect approximately 250-500 ng/ml of anti-HSA antibody in serum or plasma; preferably the assay has a limit of detection of no more than 500 ng/mL, 250 ng/mL, 150 ng/mL or 125 ng/mL of anti-HSA antibody in serum, when sample preparation including HSA removal, immunoglobulin enrichment and the bridging ELISA are performed as described herein.

It has now been found that enrichment for immunoglobulin and acidic dissociation of immunocomplexed antigens from immunoglobulin are required in order to achieve an assay that has the desired sensitivity and specificity. ELISA assays performed without these sample preparation steps typically exhibit one or more problems, such as a detection limit that is too high to be generally useful and/or high levels of non-specific binding.

In general, enriching the immunoglobulin in the sample and dissociation of immunocomplexed HSA is achieved incubating the sample with an immunoglobulin affinity substrate so that the immunoglobulin, including any immunoglobulin comprised by immunocomplexes (immunoglobulin bound to antigen) binds to the substrate, followed by elution from the substrate essentially simultaneously with acidic dissociation of any immunocomplexed antigens from the immunoglobulin. In other words, the sample is contacted with an immunoglobulin affinity substrate under conditions that permit the binding of immunoglobulin within the sample to the substrate. Elution (i.e., separation of bound immunoglobulin from the substrate) is then performed in an acidic solution, such that removal of bound immunoglobulin from the substrate occurs essentially simultaneously with acidic dissociation of immunocomplexed antigens.

While any steps that achieve enrichment for immunoglobulin and acidic dissociation of antigen may be employed, it has found, in accordance with the present invention, that the following procedure results in a sensitive and accurate assay. First, the sample is contacted with an antibody purification resin (e.g., a NAb Antibody Spin Column, available from Thermo Scientific, Waltham, Mass.) under conditions that permit binding of antibodies in the sample to the resin. The resin with bound antibodies is then washed (e.g., with Pierce IgG Binding Buffer (Thermo Scientific) or 100 mM phosphate/150 mM sodium chloride, ph 7.2) to remove unbound materials, such as HSA and other matrix proteins, which have a potential to cause interference or non-specific binding. Bound antibodies are then eluted with an acidic elution buffer (e.g., having a pH of around 3, such as a 100 mM glycine solution, pH 2.5-3.5, or the Pierce IgG elution buffer, pH 2.8, which is available from Thermo Scientific). The result is a sample that is substantially free of HSA and immunoglobulin-enriched. Because of the acidic elution buffer, the antibodies are dissociated from any previously bound antigen (i.e., immunocomplexed HSA is separated from anti-HSA antibodies). The eluate is used in a bridging ELISA without further modification. Neutralization of the eluate is not required; in fact, detection is generally enhanced if the eluate is not neutralized.

Bridging ELISA

A sample of the eluate prepared as described above is used for a bridging ELISA. Such assays involve the use of a support material to which antigen (HSA) is immobilized. One convenient support material is a 96-well plate, but it will be apparent that other supports may also be used. It has been found, within the context of the present invention, that the use of a support that allows for covalent coupling of antigen to the support decreases background signal and improves the sensitivity of the assay. Typically, such covalent coupling is achieved using a photochemical reaction that introduces a stable electrophilic group that reacts with nucleophiles such as free amines or thiol or hydroxy groups. One such support is the Nunc Immobilizer™ Amino 96-well plate (Thermo Scientific). The photocoupling reaction for this plate introduces an ethylene glycol spacer along with the electrophilic group. It will be apparent that other similar supports may also be used, such as the Pierce Amine-binding, maleic anhydride activated plate (Thermo Scientific).

It has further been found, in the context of the present invention, that even after sample preparation as described above, sufficient HSA may remain in the sample to interfere with the ELISA. This problem may be overcome by immobilizing a sufficiently high level HSA on the support. Accordingly, the covalent coupling of high levels of antigen improves assay performance. Such high levels of antigen are readily achieved by coating the support with a solution of at least 10 μg/mL of antigen (e.g., HSA); in certain embodiments, solutions of at least 20 μg/mL of antigen are used. When high levels of HSA are immobilized, the assay has a signal-to-noise ratio of at least 2.0 if the sample comprises at least 250 ng/mL anti-HSA antibody.

The support is initially coated with antigen (HSA), generally according to the manufacturer's instructions, and the unoccupied binding sites on the support are blocked. Suitable blocking solutions are known in the art, and include solutions comprising about 2% nonfat dry milk in a borate buffer (e.g., Milk Diluent/Blocking Solution, available from KPL (Gaithersburg, Md.)), as well as solutions comprising about 0.05% Tween/1% irrelevant protein (such as casein or BSA) in phosphate buffered saline (e.g., Pierce Superblock Buffer with Tween-20, available from Thermo Scientific). The sample prepared as described above is then added, along with labeled HSA and buffer sufficient to raise the pH to above 5.5 (e.g., 1 M TRIS pH 8.0) sequentially. One suitable labeled HSA is biotin-conjugated HSA, which is commercially available from, for example, Jackson ImmunoResearch (West Grove, Pa.); however, any HSA conjugated with a detectable label may be used.

After incubation for a suitable period of time at 37° C. (e.g., at least about an hour, from about 1 to about 5 hours, or about 2 hours), a detection reagent appropriate for the label is added, if needed. For biotin-HSA, a suitable detection reagent is streptavidin-conjugated horseradish peroxidase (HRP). Other suitable reagents are well known and commercially available. The support is then washed (e.g., with a solution of buffered saline and Tween, such as imidazole- or phosphate-buffered saline and Tween-20) to remove unbound label and unbound detection reagent. If a further reagent is needed to facilitate detection, such reagent is added; for the streptavidin-HRP detection reagent, tetramethylbenzidine (TMB) and hydrogen peroxide are added and color is allowed to develop for a period of time (e.g., about 20-30 minutes). The TMB and hydrogen peroxide maybe obtained commercially in combination in a single solution (e.g., SureBlue TMB 1-Component Microwell Peroxidase Substrate, available from KPL) or may be purchased in separate solutions, which are then combined before use. It will be apparent that any commercially available TMB substrate for HRP may be used. Color development is then stopped (e.g., with an acid such as 1 N sulfuric acid, or with a commercial TMB stop solution (available from KPL), and absorbance is read at 450 nm with any suitable spectrophotometer (e.g., a scanning microplate spectrophotometer, such as that available from BioTek Instruments (Winooski, Vt.) or Dynex Technologies (Chantilly, Va.)).

Within the context of the present invention, it has been unexpectedly found that the combination of sample preparation and bridging ELISA, as described herein, permit reliable measurement of sub-microgram amounts of anti-HSA antibody in human blood fluids containing very high concentrations (e.g., about 35-55 mg/mL or more) of endogenous HSA. Other conventional assays do not display this level of sensitivity and specificity. For example, a competitive indirect ELISA performed by immobilizing immunoglobulin on a Protein A/G plate (Thermo Scientific) exhibited an assay sensitivity of about 10 μg. Sandwich ELISAs using the Protein A/G plate with a labeled affibody or IgY anti-HSA antibody exhibited unacceptable non-specific binding. The addition of an acid dissociation step prior to an ELISA did not improve detection. Only the sample preparation and assay steps resulted in a suitable assay for detecting anti-HSA antibody levels in samples with high levels of HSA.

Further Methods

In other aspects, the present invention provides methods for reducing interference due to the presence of an endogenous protein counterpart (e.g., HSA) in a sample undergoing an assay. Certain such methods reduce interference due to the presence of HSA in a sample undergoing an assay such as an anti-HSA antibody screening assay, an anti-HSA antibody confirmatory assay, an anti-HSA antibody confirmatory assay, a neutralizing drug antibody assay, a biomarker assay, a drug pharmacokinetics (PK) assay, or a drug potency assay. Such methods comprise, prior to performing the assay: (a) enrichment of the immunoglobulin in the sample by incubating the sample with an immunoglobulin affinity substrate so that the immunoglobulin, including any immunoglobulin comprised by immunocomplexes binds to the substrate, followed by elution from the substrate essentially simultaneously with acidic dissociation of any immunocomplexed antigens from the immunoglobulin, to yield an immunoglobulin-enriched, antigen-dissociated sample; and (b) addition of labeled HSA and the immunoglobulin-enriched, antigen-dissociated sample to unlabeled HSA that is immobilized on a support, under conditions that result in binding of a detectable amount of labeled HSA to the support if at least 100 ng/mL or 125 ng/mL of anti-HSA antibody is present in the sample.

In other aspects, the present invention provides methods for improving sensitivity of an assay performed using a sample that comprises an endogenous protein counterpart (i.e., an endogenous protein, such as HSA, that is capable of forming immunocomplexes with an antibody of interest). Certain such methods improve sensitivity in an immunogenicity assay, a drug PK assay, a drug potency assay or a biomarker assay. Such methods comprise, prior to performing the assay: (a) enrichment of the immunoglobulin in the sample by incubating the sample with an immunoglobulin affinity substrate so that the immunoglobulin, including any immunoglobulin comprised by immunocomplexes binds to the substrate, followed by elution from the substrate essentially simultaneously with acidic dissociation of any immunocomplexed antigens from the immunoglobulin, to yield an immunoglobulin-enriched, antigen-dissociated sample; and (b) addition of labeled HSA and the immunoglobulin-enriched, antigen-dissociated sample to unlabeled HSA that is immobilized on a support, under conditions that result in binding of a detectable amount of labeled HSA to the support if at least 100 ng/mL or 125 ng/mL of anti-HSA antibody is present in the sample. In general, as noted above, a support that allows for covalent coupling of high levels of antigen improves assay performance.

Within the above methods, enrichment for immunoglobulin with acidic dissociation and the formation of immunocomplexes bound to the support may generally be performed as described above. The assays may then be performed by any suitable method; there are a variety of each of the indicated assays known in the art, and the methods provided herein may be used to reduce interference and/or improve sensitivity of any assay in which interference and/or decreased sensitivity is caused by the presence of an endogenous protein counterpart.

Kits

Also provided herein are kits for use in detecting levels of antibodies specific for an abundant antigen in a sample (e.g., anti-HSA antibody levels in a blood fluid), as described herein. Such kits typically comprise one or more substances, reagents and/or materials for use in the methods provided herein, along with instructions for performing such methods. For example, certain such kits are intended for detecting a level of anti-HSA antibody in a sample that comprises HSA.

Such a kit comprises (a) instructions that detail the processes of HSA removal, immunoglobulin enrichment, acid dissociation, and bridging ELISA, in combination with (b) one or more substances, reagents, materials or a combination thereof for use in one or more of the steps recited in the instructions. Suitable substances, reagents and materials include, for example, anti-HSA antibodies for use in controls and standards, unlabeled HSA, labeled HSA, antibody purification resin (e.g., a column such as a spin column), a multi-well plate (e.g., a 96-well plate or a 192 well plate or a 384 well plate), and buffers and/or reagents for performing the sample preparation and bridging ELISA as described herein.

In certain embodiments, a kit adapted for detecting a level of anti-HSA antibody in a sample that comprises immunoglobulin and HSA comprises instructions and, in a container, reagents for carrying out a method as described above. The reagents included may be used for one or more of (a) enriching the immunoglobulin in the sample by incubating the sample with an immunoglobulin affinity substrate so that the immunoglobulin, including any immunoglobulin comprised by immunocomplexes of immunoglobulin in the sample by incubating the sample with an immunoglobulin affinity substrate so that the immunoglobulin, including any immunoglobulin comprised by immunocomplexes binds to the substrate, followed by elution from the substrate essentially simultaneously with acidic dissociation of any immunocomplexed antigens from the immunoglobulin, to yield an immunoglobulin-enriched, antigen-dissociated sample; (b) adding labeled HSA and the immunoglobulin-enriched, antigen-dissociated sample to unlabeled HSA that is immobilized on a support, under conditions that result in binding of a detectable amount of labeled HSA to the support if at least 100 ng/mL or 125 ng/mL of anti-HSA antibody is present in the sample; (c) washing the support to remove unbound labeled HSA; and (d) detecting the amount of labeled HSA that remains bound to the support. Representative such reagents include, for example, one or more of: HSA that is immobilized on a support; labeled HSA; a wash solution; an acidic dissociation solution; and a control sample comprising immunoglobulin, HSA, and anti-HSA antibody.

The following Examples are offered by way of illustration and not by way of limitation. Unless otherwise specified, all reagents and solvents are of standard commercial grade and are used without further purification. Using routine modifications, the procedures provided in the following Examples may be varied by those of ordinary skill in the art to perform assays and make and use kits and assay components within the scope of the present invention.

EXAMPLES

Example 1

Sample Preparation

This Example illustrates the preparation of samples for use in a bridging ELISA, as described in Example 2.

Removal of HSA and enrichment for immunoglobulin is achieved using a 0.2 mL NAb protein A/G spin column (Thermo Scientific), and buffers provided therewith in the NAb spin kit available from Thermo Scientific. Every reagent and kit component, including columns, and human serum are brought to room temperature. Columns are placed in 2 mL labeled collection tubes and centrifuged at 5,000 g for 1 minute. The flow-through is discarded. Each column is then washed by adding 400 µL of Pierce IgG Binding Buffer (0.2 M, pH 7.2; prepared by dissolving the contents of one pouch provided in the NAb spin kit in a final volume of 500 mL of deionized water), mixing briefly, centrifuging the column at 5,000 g for 1 minute, and discarding the flow-through. The washing step is repeated.

The bottom of each spin column is capped with the kit-provided rubber cap, and 0.5 mL of sample is added to each column. The sample is either a clinical testing serum sample or a control sample, such as an antibody-spiked serum sample or clinical testing sample. The top of the column is capped, and columns are incubated at room temperature with end-to-end mixing for 10 minutes. The top cap is then loosened and the bottom cap is removed. Spin columns are placed in collection tubes and centrifuged for 1 minute. This first collection tube contains the non-bound sample components, which are discarded.

Each column is washed three times, each with 400 µL of Binding Buffer, as described above. 400 µL of IgG Elution Buffer (Thermo Scientific, pH 2.8) is then added to the spin columns, which are mixed and centrifuged for 1 minute to yield the first fraction of eluted antibodies. In a second set of collection tubes, 400 µL of IgG Elution Buffer is added to each spin column, which are mixed and centrifuged for 1 minute to yield the second fraction of eluted antibodies. In a third set of collection tubes, 400 µL of IgG Elution Buffer is added to each spin column, which are mixed and centrifuged for 1 minute to yield the third fraction of eluted antibodies. All three fractions of eluted antibodies for each sample are combined in one collection tube to yield a total of 1.2 mL of the eluted antibody sample from each 0.5 mL of testing sample (sample dilution factor, 1:2.4), which is ready for testing as described in Example 2.

Example 2

Bridging ELISA

This Example illustrates the detection of anti-HSA antibodies using a bridging ELISA. Each well of an Immobilizer amine 96-well plate (VWR/NUNC) is coated with 100 µL of a 20 µg/mL solution of HSA in PBS. The plate is incubated at 4° C. overnight. The coating solution is removed without washing, and the plate is blocked by adding 250 µL/well KPL milk block/diluent (prepared by diluting Milk Diluent/Blocking Solution Concentrate (KPL) 1/20 with reagent quality water (i.e., 1 mL concentration diluted with 19 mL water)). The plate is incubated for 2 hours at room temperature, at which point the blocking solution is removed without washing and the plate is blotted on a paper towel (TechniCloth, available from ITW Texwipe, Kernersville, N.C.).

A solution of biotin-conjugated human albumin (Biotin-HSA; Jackson ImmunoResearch, West grove, PA) is prepared at a concentration of 8 µg/mL in KPL milk block/diluent, and 50 µL of this Biotin-HSA solution is added to each well of the plate. 50 µL of each of the combined eluted samples from Example 1 is added to a well of the plate, followed by 15 µL of 1M TRIS pH 8.0. The plate is sealed and mixed gently on a rocker table for 5 minutes, and then incubated at 37° C. for 2 hours. The plate is then washed three times using 250 µL of 1×KPL wash buffer (prepared by diluting 20× Wash Solution Concentrate (KPL) 1:20 with water for each wash. The plate is blotted on a dry paper towel after each wash.

A solution of horse radish peroxidase (HRP)-conjugated Streptavidin (Jackson ImmunoResearch) is prepared at a concentration of 1 µg/mL in KPL milk block/diluent. 100 µL of HRP-conjugated Streptavidin is added to each well, and the plate is incubated with shaking (approx. 250 rpm) at room temperature for 45±5 minutes. The plate is then washed three times using 250 μL of 1×KPL wash solution (which contains imidazole-buffered saline and Tween-20) for each wash, and the plate is blotted on a dry paper towel after each wash.

100 μL of SureBlue TMB 1-Component Microwell Peroxidase Substrate (KPL) is added to each well at room temperature, and the plate is incubated at room temperature, protected from light, for 24 minutes. Color development is stopped by adding 100 μL of TMB STOP solution (KPL) to each well. The OD of the plate is read at 450 nm within 30 minutes.

To confirm assay sensitivity and determine the detection limit, this assay was performed using samples with different concentrations of rabbit anti-HSA antibody (ABCAM ab31657) in normal human serum. Ten samples at each concentration were assayed. The resulting data, presented in FIG. 1, show a mean cut point (CP) of 0.119, corresponding to a detection limit of 125 ng/mL.

Example 3

Clinical Application of Sample Preparation and Bridging ELISA Methods

This Example illustrates the use of the procedures described in Examples 1 and 2 to detect the presence or absence of anti-HSA antibodies in serum obtained from test subjects treated with a fusion protein that comprises a HSA sequence.

Nine human subjects were treated with B2B3-1, a bispecific antibody that comprises an HSA moiety and is described in detail in US Patent Application No. 2011/0059076, which is hereby incorporated by reference.). Serum was obtained from each subject, and samples were prepared and tested as described in Examples 1 and 2. All samples tested negative for the presence of anti-HSA antibodies. These results provide critical safety information for use in assessing candidate drugs undergoing clinical testing.

Example 4

Comparative Assays

This Example illustrates conventional assays that are unable to detect submicrogram levels of anti-HSA antibody in human serum.

A. Competitive Indirect ELISA

A competitive indirect ELISA was performed using a Protein A/G plate (Thermo Scientific). Different concentrations of anti-HSA antibody Rabbit anti-HSA antibody, ABCAM, ab31657 were spiked into assay diluent (SUPERBLOCK buffer with Tween-20, Thermo Scientific) and incubated at room temperature for 1 hour. Then the sample preparations were added to wells of the plate and incubated at room temperature for 45 minutes, so as to immobilize immunoglobulin therein. The plate was then washed with 0.1% Tween/PBS and contacted with 0.125 μg/mL of HRP-conjugated HSA, incubated for one hour, and then washed again with 0.1% Tween/PBS. TMB substrate was added and color development detected as described above.

Figure 2:
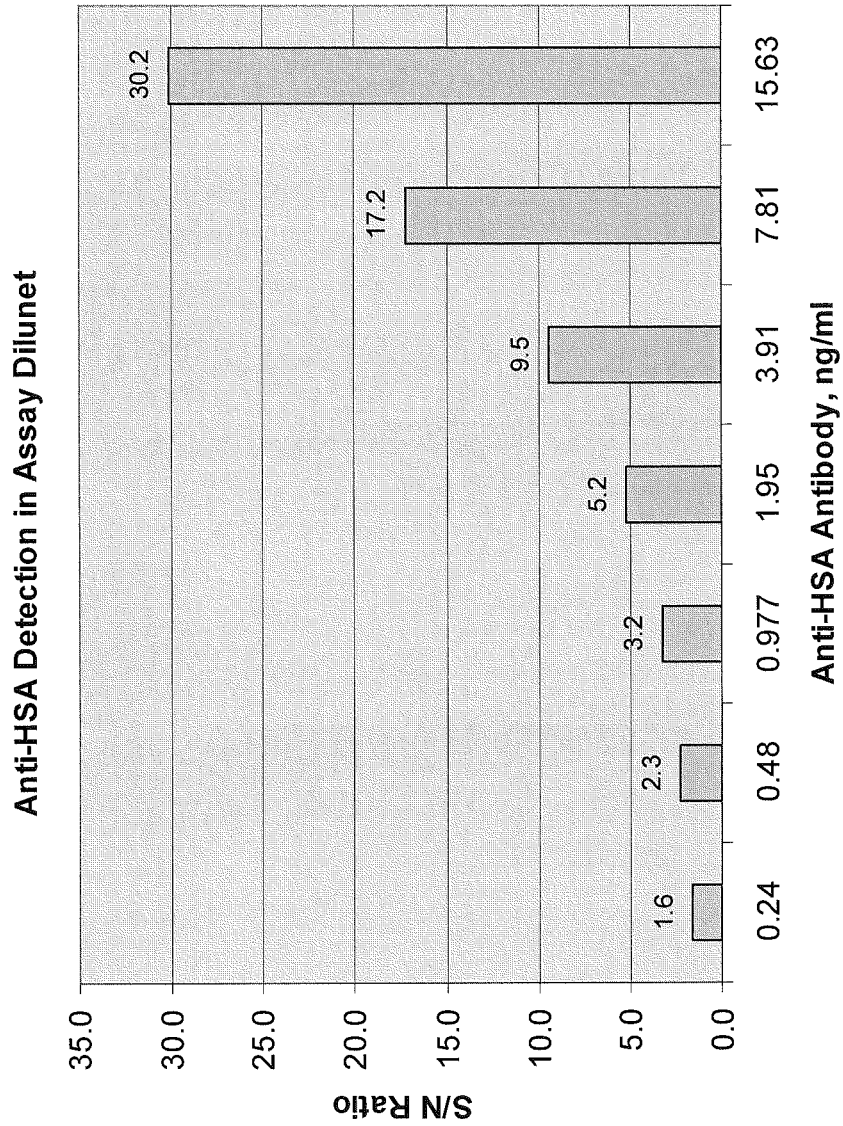
FIG. 2 is a graph showing the results (expressed a signal-to-noise ratio) of a competitive indirect ELISA of samples with different amounts of anti-HSA antibody in buffer.
Figure 3:
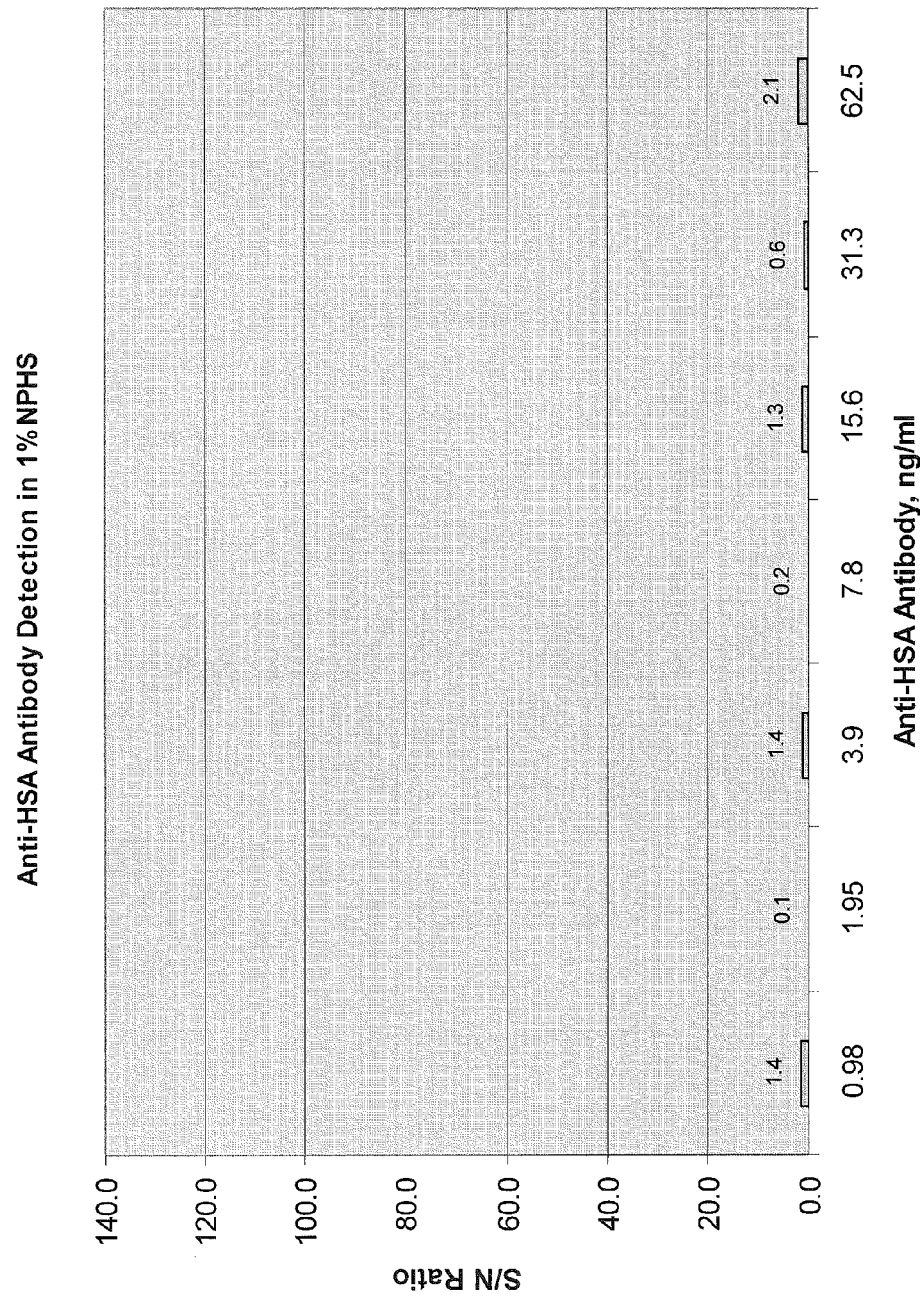
FIG. 3 is a graph showing the results (expressed a signal-to-noise ratio) of a competitive indirect ELISA of samples with different amounts of anti-HSA antibody in 1% normal human serum, in which each anti-HSA antibody sample was added to a well of a Protein A/G plate prior to incubation with labeled HSA.

In a first experiment, the anti-HSA antibody was added to assay diluent (SuperBlock buffer with Tween-20, Thermo Scientific). As shown in FIG. 2, the assay sensitivity was very high and able to detect 0.48 ng/mL anti-HSA antibody. In a second experiment, the assay was repeated in 1% pooled normal human serum, with an HSA concentration of about 300-500 μg/mL. As shown in FIG. 3, even this low level of serum was sufficient to eliminate the signal at the antibody concentrations tested.

Figure 4:
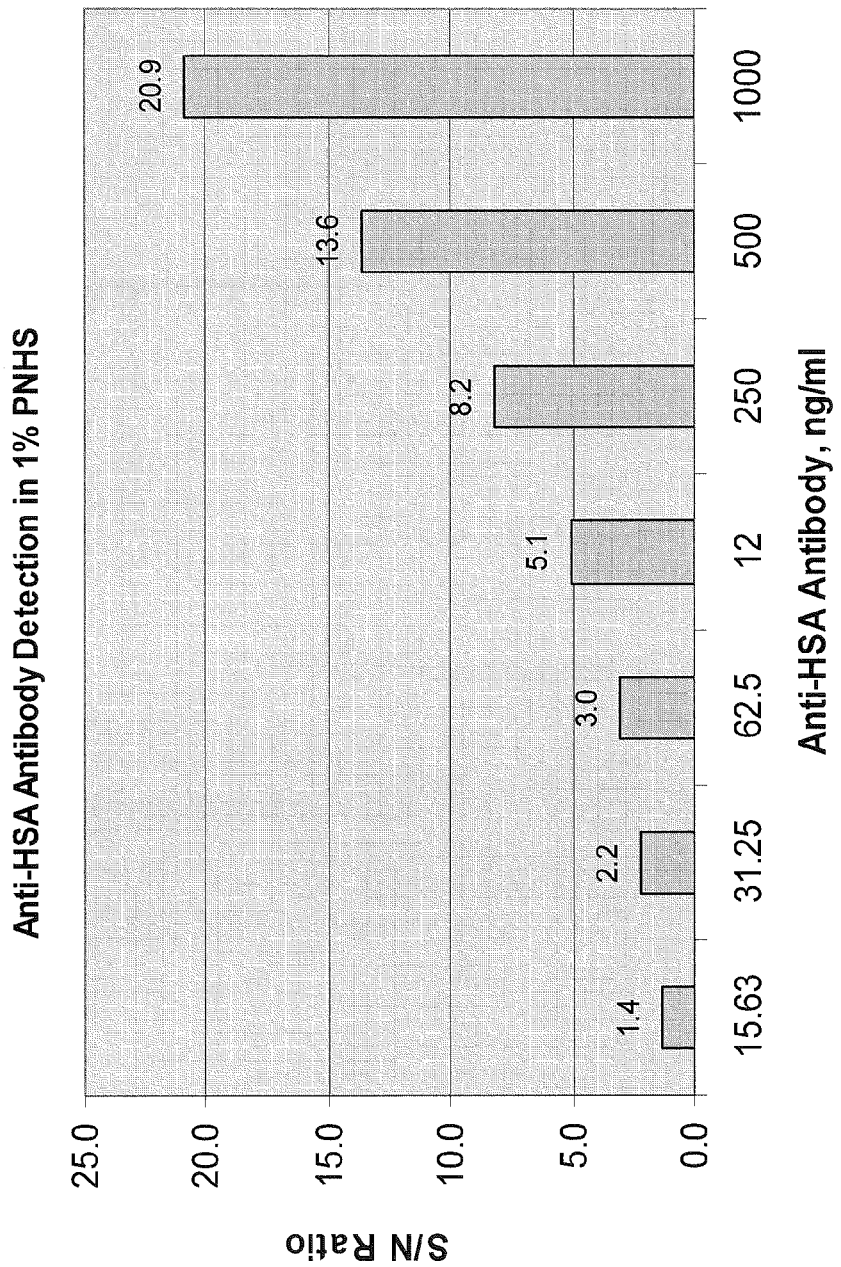
FIG. 4 is a graph showing the results (expressed a signal-to-noise ratio) of a competitive indirect ELISA of samples with different amounts of anti-HSA antibody in 1% pooled normal human serum, in which each anti-HSA antibody sample was mixed with labeled HSA and preincubated before addition to the wells of a Protein A/G plate.
Figure 5:
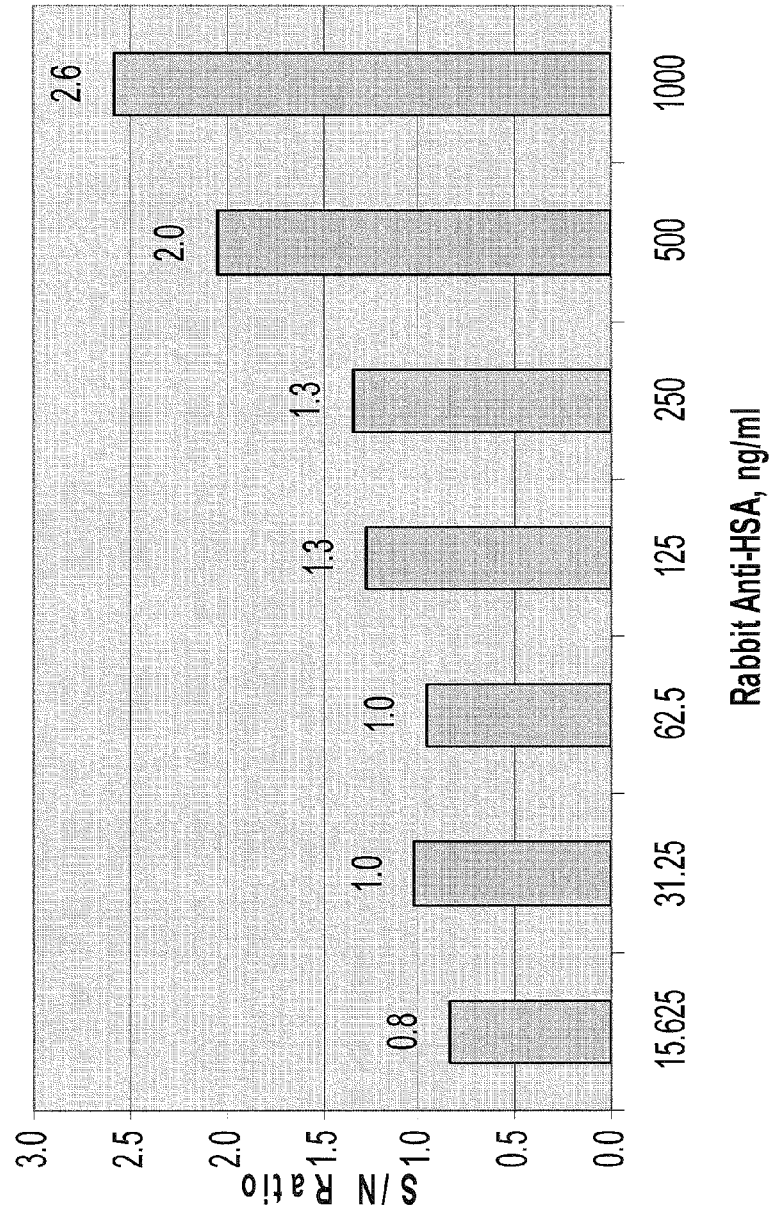
FIG. 5 is a graph showing the results (expressed a signal-to-noise ratio) of a competitive indirect ELISA of samples with different amounts of anti-HSA antibody in neat human serum.

In a third experiment, using samples of anti-HSA antibody in 1% pooled normal human serum, the format was revised. The anti-HSA antibody in 1% pooled normal human serum was mixed with 4 μg/mL of HRP-conjugated HSA. The mixture was incubated for 2 hours at 37° C. to allow HRP-labeled HSA to replace HSA in HSA/anti-HSA immune complexes, and then added to the Protein A/G plate and incubated at room temperature for 45 minutes. Detection as described above resulted in an assay with a detection limit of about 3 μg/mL (30 ng/mL×100 dilution factor; FIG. 4). However, a similar assay performed in neat human serum to mimic clinical sample condition exhibited an assay sensitivity of about 10 μg/mL (500 ng/mL×20 (dilution factor); see FIG. 5). In this assay different amounts of anti-HSA antibody were added to neat human serum and incubated at room temperature for 1 hour. The samples were then diluted 1:10 with SuperBlock buffer with Tween-20, mixed 1:1 with 7.5 μg/mL of HRP-conjugated HSA, incubated at 4° C. overnight, added to the wells of a Protein A/G plate, and incubated at room temperature for 45 minutes. The results following detection as described above, presented in FIG. 5, indicate that this assay is not suitable for detecting anti-HSA antibody in human serum.

B. Sandwich ELISA Using Affibody or IgY Antibody

Figure 6:
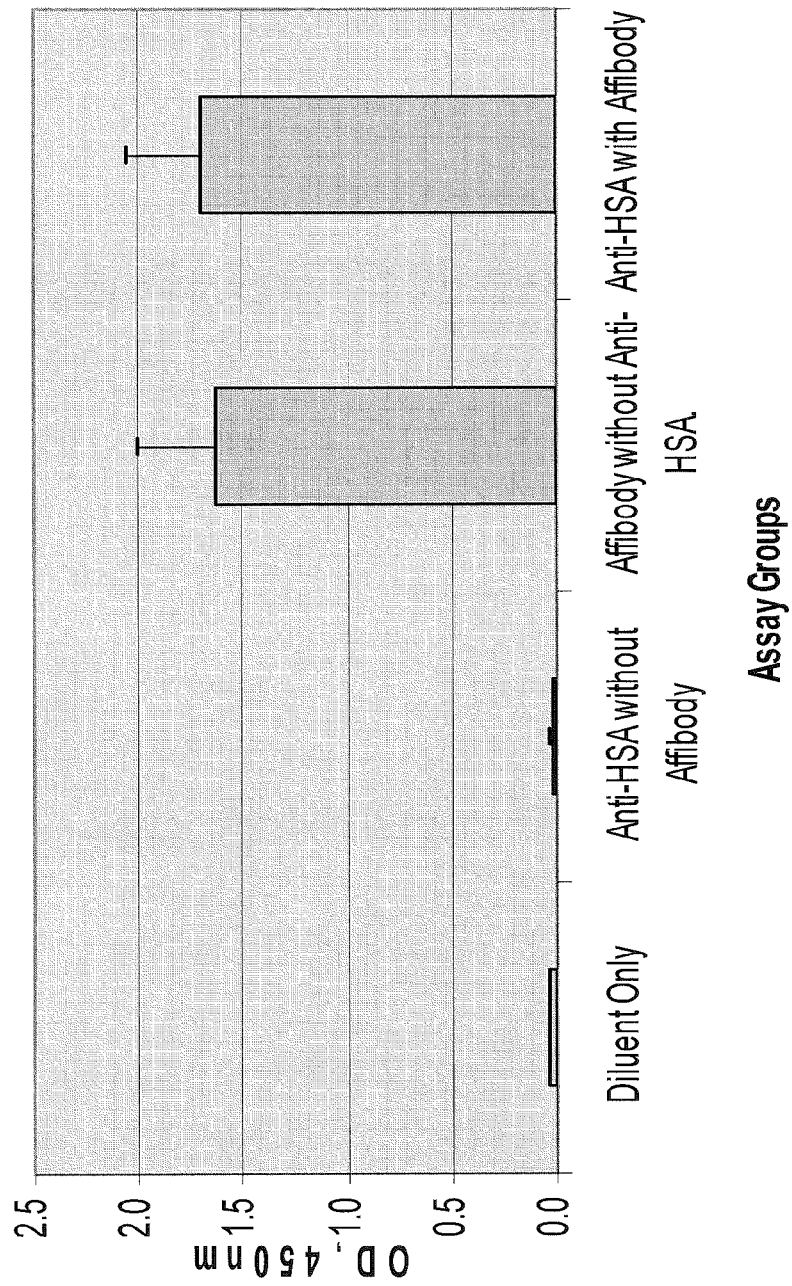
FIG. 6 is a graph showing the results (expressed as OD at 450 nm) of a sandwich ELISA of samples with different amounts of anti-HSA antibody in 1% pooled normal human serum, in which an affibody is used for immunocomplex detection.

In this assay, different concentrations of anti-HSA antibody were spiked into 1% pooled normal human serum to form HSA/anti-HSA immune complex, added to wells of a Protein A/G plate and incubated at room temperature for 45 minutes on shaker at 250 rpm. Free HSA was then removed by washing with 0.1% Tween/PBS, and biotin-conjugated anti-HSA affibody (ABCAM, ab31898) was added. Following incubation at room temperature for 1 hour and washing with 0.1% Tween/PBS, HRP-conjugated streptavidin was added and incubated at room temperature for 30 minutes. After washing with 0.1% Tween/PBS, TMB was added and color developed as described above. The results indicate that the affibody results in unacceptably strong non-specific binding (FIG. 6).

Figure 7:
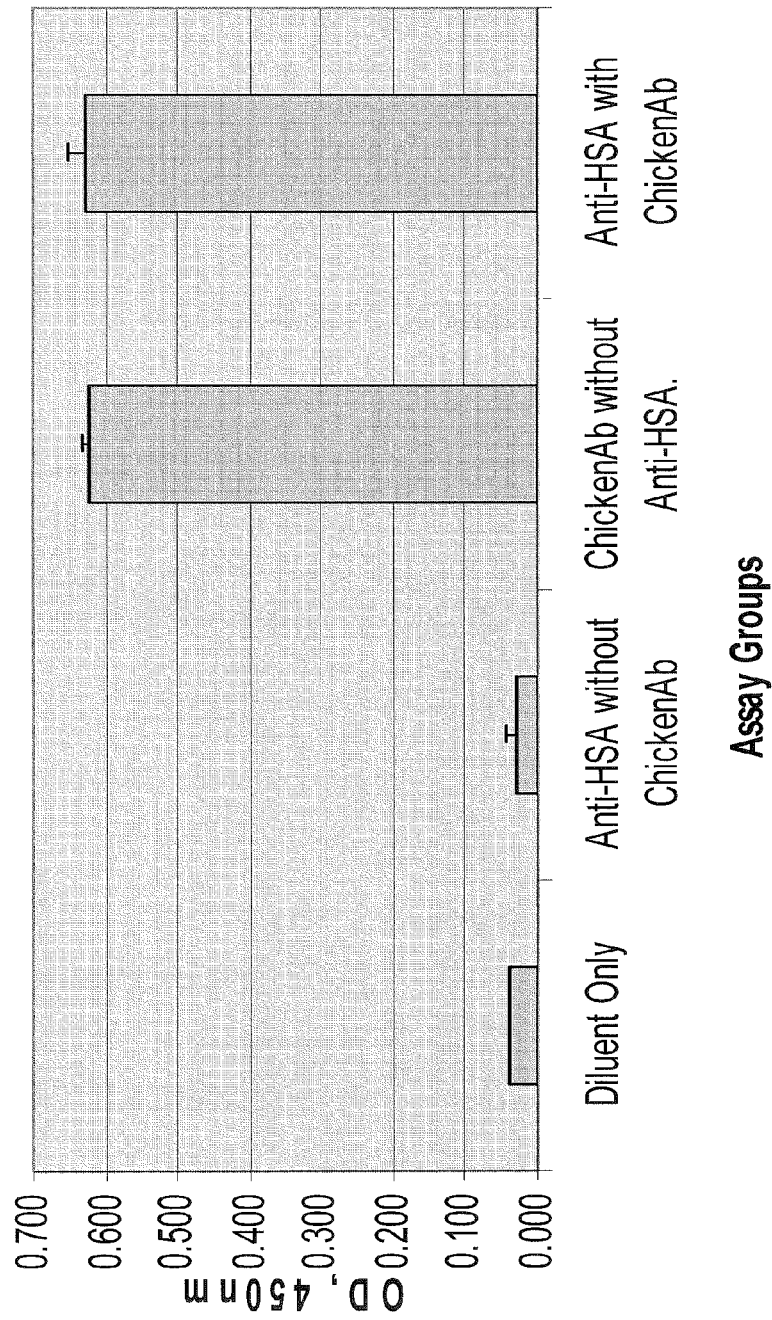
FIG. 7 is a graph showing the results (expressed as OD at 450 nm) of a sandwich ELISA of samples with different amounts of anti-HSA antibody in 1% pooled normal human serum, in which an anti-HSA IgY is used for immunocomplex detection.

In a similar assay, a chicken anti-HSA IgY antibody (ABCAM ab63500) was used instead of the affibody. The results of this experiment also showed an unacceptable level of non-specific binding (FIG. 7).

C. ELISA with Acid Dissociation

Figure 8:
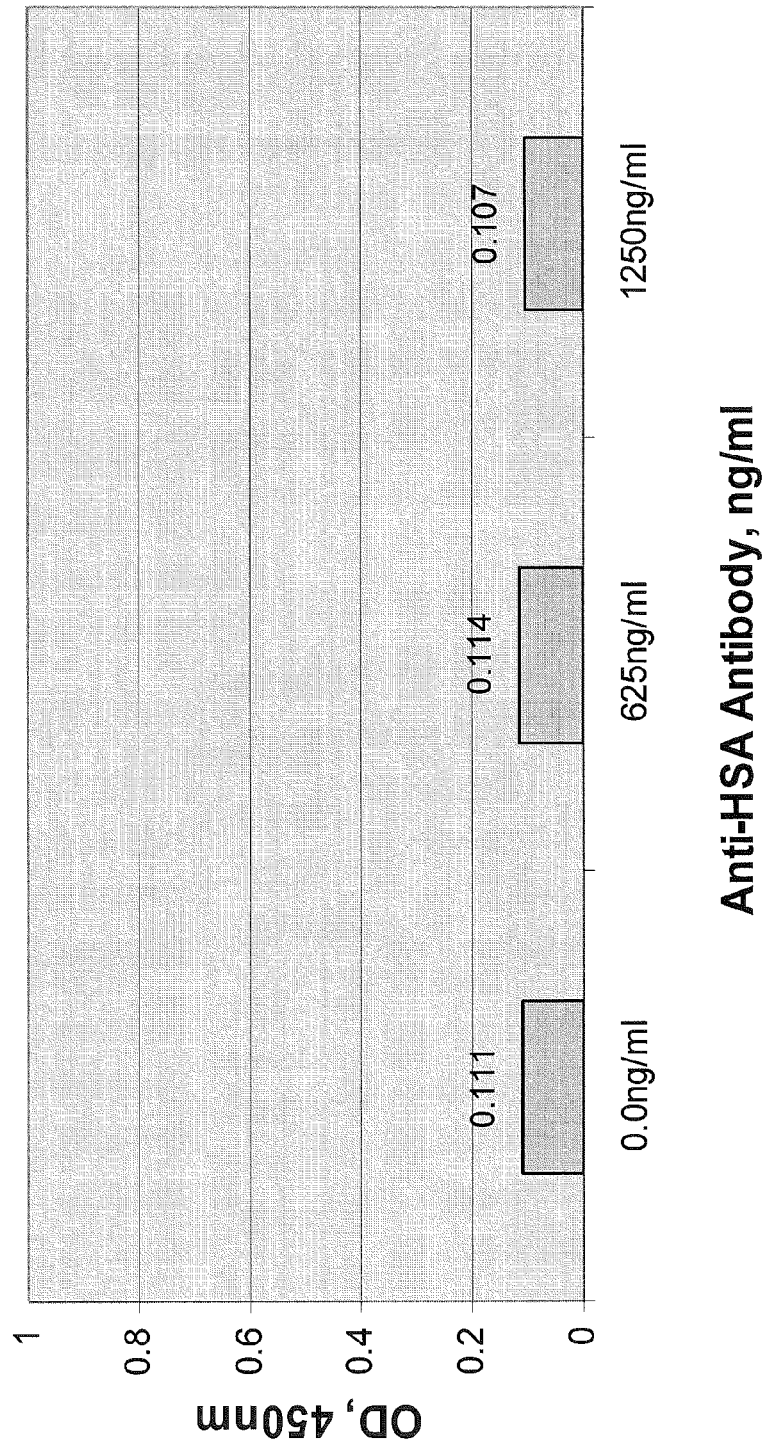
FIG. 8 is a graph showing the results (expressed as OD at 450 nm) of an ELISA of samples with different amounts of anti-HSA antibody in 1% pooled normal human serum, after pretreatment with 300 mM acetic acid for 60 minutes at room temperature, and neutralization with 1.0 M Tris base.

Sixteen μg/mL of anti-HSA antibody (Rabbit anti-HSA antibody, ABCAM ab31657) were added to neat serum and incubated at room temperature for 1 hour to mimic clinical sample conditions. Final concentrations of anti-HSA antibody in the samples were 625 and 1250 ng/mL. The samples were then treated with acid (300 mM acetic acid at room temperature for 1 hour). The acidified samples were added to an HSA pre-coated and KPL milk diluent pre-blocked Immobilizer plate, along with 1.0 M Tris and 8 μg/ml of biotin-conjugated HSA and incubated at 4° C. overnight. After washing as described above, HRP-conjugated streptavidin was added, samples were incubated and washed, TMB substrate was added and detection was as described above. The results revealed no significant difference in signal between the samples with and without added anti-HSA antibody, which indicated that using this dissociation method, anti-HSA antibody could not be detected in samples containing high levels of endogenous HSA (FIG. 8).

Example 5

Effect of HSA Coating Density on Detection of Anti-HSA Antibody

This Example illustrates the effect of varying the coating density of HSA on the support on the detection limit for anti-HSA antibody in neat human serum.

Figure 9:
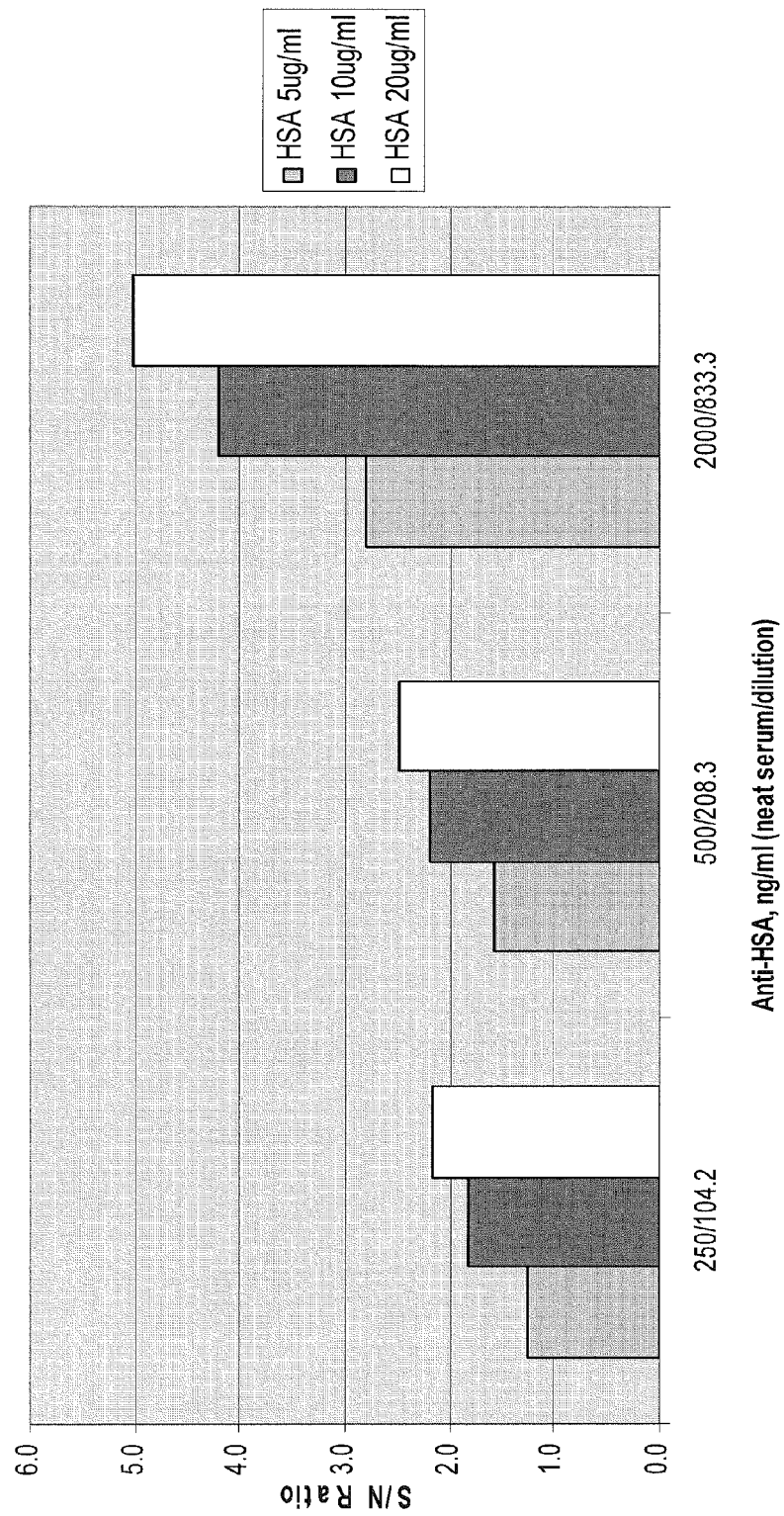
FIG. 9 is a graph showing the results (expressed as signal-to-noise ratio) of bridging ELISAs performed on samples of neat serum to which the indicated amounts of anti-HSA antibody were added, and illustrating the effect of varying the concentration of HSA used to coat the solid support.

Anti-HSA antibody was added to samples of neat human serum to a final concentration of 250 ng/mL, 500 ng/mL and 1000 ng/mL. Samples were then prepared as described in Example 1 and a bridging ELISA was performed as described in Example 2, except that three different concentrations of HSA were used to coat the plate: 5 μg/mL, 10 μg/mL and 20 μg/mL. The results of the assay are presented in FIG. 9 as signal-to-noise ratio (S/N) for each of the three HSA concentrations and each of the three antibody concentrations. The higher concentration of HSA (i.e., the higher capture density) resulted in a higher S/N ratio. Using the higher concentration of HSA, the limit of detection was 250 ng/mL in neat serum.

Example 6

High-Throughput Sample Preparation

This example illustrates a robust, high-throughput implementation of the sample preparation paradigm detailed in Example 1. High throughput, automated preparation of samples is desirable to reduce labor, improve assay consistency, and allow analysis of large numbers of samples. This high throughput sample preparation method is carried out using the following protocol, which may be readily modified for automated practice.

1. Remove Protein G 96-well Spin Plate (ThermoScientific, Catalogue #45204) and buffers (Binding buffer, BupH™ PBS Buffer, ThermoScientific, Catalogue #28372; Elution buffer, IgG Elution Buffer, ThermoScientific, Catalogue #21004) from storage and place on bench top at ambient room temperature for at least 30 minutes.
2. Remove the seal from the bottom of the Protein G 96-well Spin plate and place plate on top of wash plate to yield a plate assembly.
3. Pre-load: 100 μL of samples (including Positive Controls (PCs) spiked with anti-HSA antibodies) to appropriate wells of Polypropylene Reagent Preparation Plate.
4. Wash plate: remove the top seal. Add 200 μL of Binding buffer to each well of Protein G Spin plate. Centrifuge plates (assembly) at 1000×g for 1 minute at ambient temperature, discard flow-through and repeat this step.
5. Load: Transfer 500 μL of samples (including PCs) from Polypropylene Reagent Preparation Plate (Biolynx Catalogue # GR650201) to appropriate wells of Protein G 96-well Spin plate. Note: Load samples into center of gel bed and expel entire volume by touching pipette tip to gel bed.
6. Cover the top plate with a plate sealer. Incubate the plate assembly on a plate shaker set at 200 rpm, in an incubator set at 20.5° C. for 30 minutes (+2 minutes).
7. Centrifuge plate assembly at 1000×g for 1 minute at ambient temperature, take separate plates of plate assembly discard flow-through.
8. Replace Protein G 96-well Spin Plate on top of the wash plate, add 500 μL of binding buffer to each well and then Centrifuge plates (assembly) at 1000×g for 1 minute at ambient temperature, discard flow-through and repeat this step 3 more times and then remove and discard wash plate.
9. Place Protein G 96-well Spin Plate on top of the collection plate (Collection plate #1) to yield a plate assembly, align plates so that wells A1 of both plates are aligned
10. Elution #1: Add 200 μL of Elution buffer to all wells of a Protein G 96-well plate, cover with a plate sealer. Incubate on a plate shaker set at 200 rpm, in an incubator at 20.5° C. for 1 to 3 minutes.
11. Centrifuge plate assembly at 1000×g for 1 minute at ambient temperature, separate plates, reserve collection plate (containing flow-through) and assemble Protein G plate with fresh collection plate as a plate assembly.
12. Repeat 10 and 11 a total of three times.
13. Pool all volume from each corresponding well of the three reserved collection plates into the corresponding wells of a 96-deep well plate. Mix each well by pipetting up and down.

Example 7

High-Throughput Bridging ELISA

B2B3-1 (MM-111) is a bispecific scFv antibody fusion molecule comprising B1D2, a human anti-ErbB2 scFv antibody and H3, a human anti-ErbB3 scFv. The two scFvs are joined by a modified human serum albumin (HSA) linker. The following anti-B2B3-1 antibody screening electrochemiluminescence assay uses a bridging format that eliminates the need for species-specific secondary antibodies and detects all classes of immunoglobulins. The assay is dependent on bivalent binding of anti-B2B3-1 antibodies to both biotin- and (ruthenium) Sulfo Tag-labeled B2B3-1 protein. Therefore, in the presence of anti-drug antibodies (ADA), a complex will form between biotin-labeled drug, anti-B2B3-1 antibodies (the analyte) and Sulfo-Tag-labeled drug. The complex is bound to Streptavidin-coated plate through biotin and Streptavidin interaction and detected via the Sulfo-Tag-labeled drug, which produces light [electrochemiluminescence (ECL)] on application of an electric potential, measured on an MSD (Meso Scale Discovery, Gaithersburg Md.) SECTOR™ Imager Reader.

| Materials | | |
|---|---|---|
| Identity | Suppliers | Cat. # |
| Anti-B2B3-1 | Merrimack | N/A |
| B2B3-1 | Merrimack | N/A |
| B2B3-1-Biotin | Merrimack | N/A |
| B2B3-1-SulfoTag | Merrimack | N/A |
| Pooled normal human Serum | Bioreclamation LLC | HMSRM |
| Individual human serum lots | Bioreclamation | HMSRM |
| MSD Standard Streptavidin plate | MSD | L15SA-1 |
| DPBS without Magnesium or Calcium | Biowhittaker/Lonza | 17-512Q |
| 10XPBS Liquid Concentrate, 4 L | EMD Chemicals (Gibbstown, NJ) | 6505 |
| Tween 20 | Sigma | P7949-500 ml |
| Acid, 300 mM Acetic Acid | Merrimack (9 ml Acetic Acid in 500 ml H$_2$O) | N/A |
| 1.5M Tris Base, pH 10 (Prepared from Tris Base) | | JT Baker X171-03 |
| MSD Reading Buffer T (4X) with surfactant, 1 L/bottle | MSD | R92TD-1 |
| AccuGENE Molecular Biology Grade Water | LONZA | 51200 |

-continued

| Materials | | |
|---|---|---|
| Identity | Suppliers | Cat. # |
| NUNC 0.5 ml round-bottom 96-well polyproplyne plate | Thermo Fisher, | 267245 |
| 30% Albumin solution from bovine serum | Sigma | A9576-50 ML |
| Sector Imager | MSD | 2400 |

Reagent Preparation

Preparation of Blocking Buffer (3% BSA/PBS): 1.6 ml of 30% BSA solution is mixed with 14.4 ml of PBS buffer in a 50 ml centrifuge tube. Other volumes may be made using this same ratio of components. Blocking buffer is prepared on the day of use. A 16 ml volume is used for each plate.

Preparation of Washing Buffer (PBST, 0.05% Tween/PBS): 0.5 ml of Tween 20 is mixed with 1 L of 1×PBS. Buffer is stored at room temperature until needed.

Preparation of Assay Diluent (PBSTB, 1% BSA/PBST): 1 ml of 30% BSA solution is mixed with 29 ml of PBST in a 50 ml centrifuge tube. Other volumes may be made using this same ratio of components.

Methods

All reagents are brought to room temperature and buffers are prepared as described above. Anti-MM-111 antibody mock samples are prepared as follows: A 2× concentrated anti-B2B3-1 in 100% human serum solution and a 2× concentrated B2B3-1 in 100% human serum solution are prepared. The 2× concentrated anti-B2B3-1 is then mixed with either the 2× concentrated B2B3-1 or 100% serum at a 1:1 ratio. The mock samples are transferred to Reagent Preparation Plate 1 (a 96-well polypropylene plate is used as the reagent preparation plate.). The plate is then incubated at room temperature for 1 hour with shaking at Speed #5 using Titer Plate Shaker (Lab-Line Instruments). This shaker speed is used for all steps in the assay.

Streptavidin (SA) plates are incubated with blocking buffer by adding 150 µl 3% BSA/PBS to each well. The plate is blocked at room temperature (RT) for 2 hours with shaking.

Samples are then acid treated by adding 180 µl acid to each well of Reagent Preparation Plate 2. 20 µl of sample was transferred from each well of Reagent Preparation Plate 1 to each well of Reagent Preparation Plate 2. Samples are incubated for 30 minutes at room temperature with shaking.

For labeled drug samples (LD) a 2× concentration of Biotin-B2B3-1 in PBSTB (2 µg/ml) and a 2× concentration of Sulfo-TAG-B2B3-1 in PBSTB (6 µg/ml) is prepared. 450 of 2× concentrated Biotin-B2B3-1 and 45 µl of 2× concentrated Sulfo-TAG-B2B3-1 is added to each well of Reagent Preparation Plate 3.

50 µl acid-treated mock samples from each well of Reagent Preparation Plate 2 is transferred to each well of Reagent Preparation Plate 3 (LD Plate) and 10 µl Tris is added to each well. The plate is neutralized at room temperature for two hours at room temperature with shaking and protection from light.

Blocking buffer is removed from the SA plate and the plate is washed twice with 150 µl washing buffer per well. 50 µl per well of neutralized samples from Reagent Preparation Plate 3 is transferred to each well of the blocked MSD SA plate. The plate is sealed and incubated at room temperature for 2 hours with shaking and protection from light.

After the incubation, samples are removed from the MSD SA plate and washed four times with 150 µl washing buffer per well. 150 µl MSD Read Buffer is added to each well and the plate is read immediately on a MSD Sector Imager 2400 or equivalent.

Example 8

Results

Figure 10:
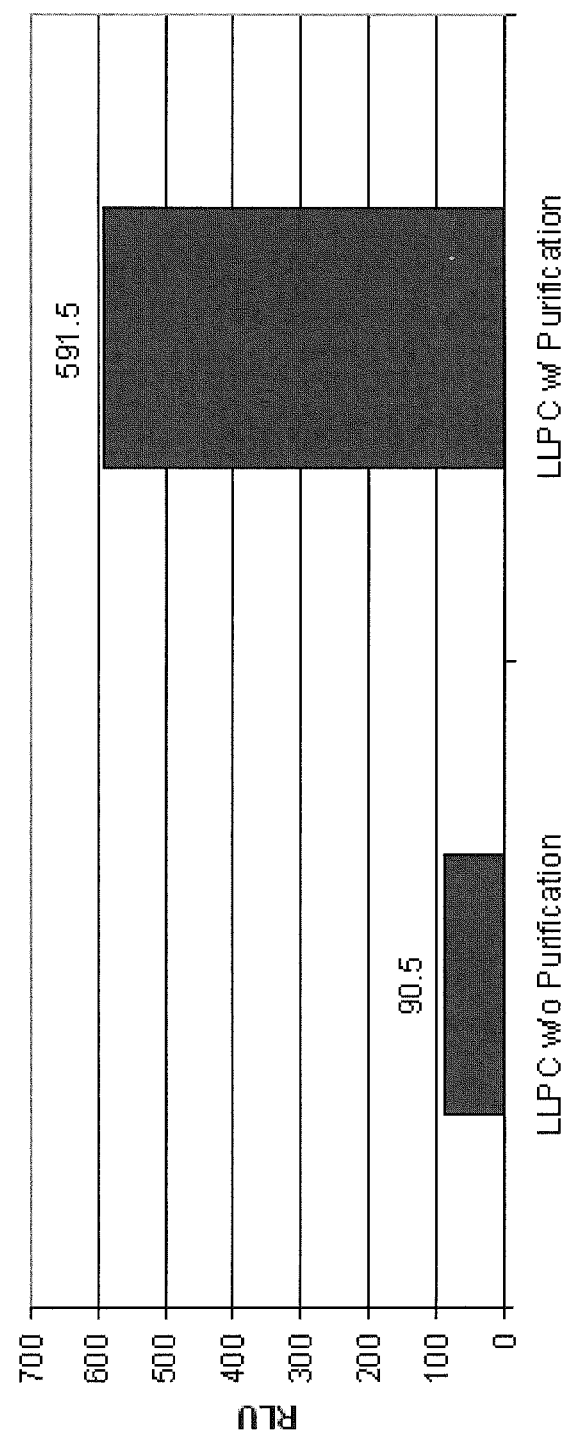
FIG. 10 shows the results of the experiments set forth in Example 8. RLU=Relative Luminescence Units. LLPC w/o Purification indicates results obtained using low level positive control samples that were not subjected to preparation according to Example 6. LLPC w/Purification indicates results obtained using low level positive control samples that were prepared according to Example 6.

Sample preparation was performed, using the methods described in Example 6 or minor variations thereof, on Low Level Positive Control (LLPC) samples. LLPC samples contain 250 ng/ml of anti-drug antibody (ADA) in neat serum, and because of the very high HSA levels in neat serum, essentially all off of the ADA in LLPC is immunocomplexed with HSA. Bridge ELISAs were performed using the methods described in Example 7 or minor variations thereof. ELISAs were also performed on LLPC samples that were not prepared using Protein G 96-well Spin Plate Purification. ELISA data thus generated are presented in FIG. 10. The ELISA signal of the LLPC sample that was not subjected to sample preparation according to Example 6 (without Protein G 96-well Spin Plate purification) was very low at 90.5 Relative Luminescence Units (RLU), while sample preparation according to Example 6 dramatically increased (6.5-fold higher-591.5 RLU) the LLPC ELISA signal. The data in FIG. 10 represent mean results from two independent experiments.

The invention claimed is:

1. A method for measuring a level of anti-HSA antibody in a sample, the method comprising analyzing a sample that wherein the sample comprises immunoglobulin and HSA,
   and the sample further comprises human serum or human plasma;
   and the sample further comprises either a drug comprising HSA or a fragment of at least 50 contiguous amino acids thereof, or
   the sample comprises a drug comprising an HSA sequence that is at least 90% identical to the HSA sequence recited in SEQ ID NO:1,
   wherein the sample is obtained from a human to whom the drug was previously administered,
   the method analysis comprising:
   (a) enriching the immunoglobulin in the sample by incubating the sample with an immunoglobulin affinity substrate so that the immunoglobulin, including any immunoglobulin comprised by immunocomplexes binds to the substrate, followed by elution of immunoglobulin from the substrate essentially simultaneously with acidic dissociation of any immunocomplexed antigens from the immunocomplexes, to yield an immunoglobulin-enriched, antigen-dissociated sample;
   (b) adding labeled HSA and the immunoglobulin-enriched, antigen-dissociated sample to unlabeled HSA that is immobilized on a support, under conditions that result in indirect binding of a detectable amount of labeled HSA to the support if at least 125 ng/mL of anti-HSA antibody is present in the sample;
   (c) washing the support to remove unbound labeled HSA; and
   (d) detecting the amount of labeled HSA that remains bound to the support;
   wherein the amount of labeled HSA detected is indicative of the level of anti-HSA antibody in the sample,
   wherein the detecting has a signal-to-noise ratio of at least 2.0 if the sample comprises at least 250 ng/mL anti-HSA antibody.

2. A method according to claim 1, wherein the sample comprises a drug comprising HSA or a fragment of at least 50 contiguous amino acids thereof.

3. A method according to claim 1, wherein the drug comprises an HSA sequence that is at least 90% identical to the HSA sequence recited in SEQ ID NO:1.

4. A method according to claim 1, wherein enriching the sample for immunoglobulin is achieved using an antibody purification resin.

5. A method according to claim 1, wherein the acidic solution has a pH that ranges from 2.5 to 3.5.

6. A method according to claim 1, wherein the HSA that is immobilized on the support is covalently bound to a polymeric support.

7. A method according to claim 6, wherein the HSA is immobilized on the support by contacting the support with a solution of at least 10 µg/mL HSA at 37° C. for at least 1 hour.

8. A method according to claim 1, wherein the labeled HSA is biotin-conjugated HSA and wherein the detection of an amount of labeled HSA that is bound to the support is achieved by adding horse radish peroxidase-conjugated streptavidin and tetramethylbenzidine to the bound immunocomplexes under conditions that permit the binding of streptavidin to the biotin, and removing unbound horse radish peroxidase-conjugated streptavidin; and detecting an amount of bound horse radish peroxidase activity; and therefrom determining the level of labeled HSA that is bound to the support.

* * * * *